United States Patent
Bae et al.

(10) Patent No.: US 10,232,091 B2
(45) Date of Patent: Mar. 19, 2019

(54) STENT FOR INHIBITING RESTENOSIS AND STIMULATING REENDOTHELIALIZATION PREPARED BY FEMTOSECOND LASER PROCESSING AND METHOD OF PREPARING THE SAME

(71) Applicants: Chonnam National University Hospital, Gwangju (KR); JEONNAM TECHNOPARK, Jeollanam-do (KR)

(72) Inventors: In Ho Bae, Gwangju (KR); Dae Sung Park, Gwangju (KR); So Youn Lee, Gwangju (KR); Eun Jae Jang, Gwangju (KR); Jae Won Shim, Gwangju (KR); Kyung Seob Lim, Gwangju (KR); Jun Kyu Park, Gwangju (KR); Kwang Hwan Oh, Gwangju (KR); Myung Ho Jeong, Gwangju (KR)

(73) Assignees: CHONNAM NATIONAL UNIVERSITY HOSPITAL, Gwangju (KR); JEONNAM TECHNOPARK, Jeollanam-Do (KR)

( * ) Notice: Subject to any disclaimer, the term of this patent is extended or adjusted under 35 U.S.C. 154(b) by 0 days.

(21) Appl. No.: 15/391,067

(22) Filed: Dec. 27, 2016

(65) Prior Publication Data

US 2017/0182227 A1    Jun. 29, 2017

(30) Foreign Application Priority Data

Dec. 24, 2015  (KR) .................. 10-2015-0186787

(51) Int. Cl.
*A61F 2/00*   (2006.01)
*A61F 2/82*   (2013.01)
(Continued)

(52) U.S. Cl.
CPC ............ *A61L 31/10* (2013.01); *A61F 2/0077* (2013.01); *A61F 2/82* (2013.01); *A61L 31/14* (2013.01);
(Continued)

(58) Field of Classification Search
None
See application file for complete search history.

(56) References Cited

U.S. PATENT DOCUMENTS 8,461,478 B2   6/2013  Chen et al.
8,679,520 B2   3/2014  Horres et al.
(Continued)

FOREIGN PATENT DOCUMENTS

JP  2005-095610 A  4/2005
KR  2004-0050915 A  6/2004
KR  10-2012-0131528 A  12/2012

OTHER PUBLICATIONS

Smith et al., "Advances in Femtosecond Micromachining and Inscription of Micro and Nano Photonic Devices", Frontiers in Guided Wave Optics and Optoelectronics, Intech, 2010, pp. 295-320.*

(Continued)

*Primary Examiner* — Carlos A Azpuru
*Assistant Examiner* — Casey S Hagopian
(74) *Attorney, Agent, or Firm* — Leydig, Voit & Mayer

(57) ABSTRACT

Provided are a stent in which a surface of a stent strut is treated by femtosecond laser radiation and is modified by a natural polymer and a method of preparing the stent. The stent and the preparing method may inhibit restenosis and stimulate reendothelialization.

7 Claims, 8 Drawing Sheets

(51) Int. Cl.
*A61L 31/10* (2006.01)
*A61L 31/14* (2006.01)
(52) U.S. Cl.
CPC . *A61F 2002/0081* (2013.01); *A61F 2002/825* (2013.01); *A61F 2240/001* (2013.01); *A61L 2400/18* (2013.01); *A61L 2420/02* (2013.01)

(56) References Cited

U.S. PATENT DOCUMENTS

| | | | | |
|---|---|---|---|---|
| 2002/0004679 A1* | 1/2002 | Eury | ............... | A61K 31/47 623/1.15 |
| 2005/0070996 A1* | 3/2005 | Dinh | ............... | A61F 2/91 623/1.42 |
| 2007/0212388 A1* | 9/2007 | Patravale | ............... | A61K 31/337 424/422 |

OTHER PUBLICATIONS

Definition of "Incubate," fom www.dictionary.com/browse/incubate, printed May 30, 2017.

* cited by examiner

STENT FOR INHIBITING RESTENOSIS AND STIMULATING REENDOTHELIALIZATION PREPARED BY FEMTOSECOND LASER PROCESSING AND METHOD OF PREPARING THE SAME

CROSS-REFERENCE TO RELATED APPLICATION

This application claims the benefit of Korean Patent Application No. 10-2015-0186787, filed on Dec. 24, 2015, in the Korean Intellectual Property Office, the disclosure of which is incorporated herein in its entirety by reference.

BACKGROUND

Field

One or more embodiments relate to a stent for inhibiting restenosis and stimulating reendothelialization, and a method of manufacturing the stent.

Description of the Related Art

A coronary heart disease (CHD) is a disease which occurs in the blood vessels around the heart, causing blood supply failure to cardiac muscles. Treatments of coronary heart diseases include bygraft surgery to transplant new blood vessels, balloon angioplasty, stenting, and the like.

A stent is a cylindrical, tubular precision medical device used to normalize blood flow failure by being inserted into a narrowed or clogged blood vessel site resulting from the clogging of blood vessels due to a disease or blood clots (thrombi). Stenting is more convenient than surgical treatments, and leads to a reduced restenosis incidence than that of balloon angioplasty, and thus recently is increasingly used.

However, about 20% of the patients who had stenting was found to have neointimal hyperplasia and restenosis that blood vessel narrowing occurs again, due to excessive proliferation of smooth muscle cells around the stent. When a bare metal stent is inserted, this stent may be completely covered by endothelial cells in a predetermined time from the insertion and not exposed within the blood vessel (reendothelialization). However, when a drug-eluting stent is inserted, this stent may not be covered by endothelial cells and be exposed within the blood vessel, causing platelet aggregation and consequential stent thrombosis.

Therefore, there is a need to develop a stent for inhibiting restenosis and stimulating reendothelialization.

SUMMARY

One or more embodiments include a stent for inhibiting restenosis and stimulating reendothelialization.

One or more embodiments include a method of manufacturing the stent for inhibiting restenosis and stimulating reendothelialization.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
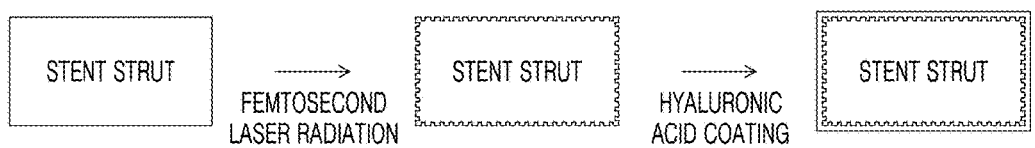
FIG. 1A is a schematic view illustrating a method of preparing a femtosecond laser-irradiated and hyaluronic acid-coated stent according to an embodiment, and FIG. 1B exhibits scanning electron microscope (SEM) images of femtosecond laser-irradiated and/or hyaluronic acid-coated stents.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present disclosure, there is provided a stent in which a surface of a stent strut is treated by femtosecond laser radiation and is modified by a natural polymer.

The femtosecond refers to a unit of time equal to $10^{-15}$ of a second. The femtosecond laser refers to a laser that emits ultrashort pulses of light with a pulse duration on the order of femtoseconds.

The stent may have at least one groove on the femtosecond laser-irradiated) surface thereof. The groove may be a hole, slot, slit. The groove may have a diameter of about 1 μm to about 100 μm, and in some embodiments, about 2 μm to about 80 μm, and in some other embodiments, about 3 μm to about 60 μm, and in some other embodiments, about 4 μm to about 40 μm, and in still other embodiments, about 5 μm to about 20 μm, and in yet still other embodiment, about 10 μm. The groove may have a depth of about 0.01 μm to about 100 μm, and in some embodiments, about 0.02 μm to about 50 μm, and in some other embodiments, about 0.03 μm to about 10 μm, and in some other embodiments, about 0.04 μm to about 5 μm, and in some other embodiments, about 0.05 μm to about 1 μm, and in still other embodiments, about 0.06 μm to about 0.5 μm, and in yet still other embodiments, about 0.1 μm.

The natural polymer may be at least one selected from the group consisting of hyaluronic acid, alginic acid, pectin, carrageenan, chondroitin sulfate, dextran sulfate, chitosan, polylysine, collagen, gelatin, carboxymethylchitin, fibrin, dextran, agarose. pullulan, polyacrylamide (PAAm), poly (N-isopropylacrylamide-co-acrylic acid) (P(NIPAAm-co-AAc)), poly(N-isopropylacrylamide co-ethyl methacrylate) (P(NIPAAm-co-EMA)), polyvinyl acetate/polyvinyl alcohol (PVAc/PVA), poly(N-vinylpyrrolidone) (PVP), poly(methyl methacrylate-co-hydroxyethyl methacrylate) (P(MMA-co-HEMA)), poly(polyethylene glycol-co-peptide) (P(PEG-co-peptide)), alginate-g-(polyethylene oxide-polypropylene oxide-polyethylene oxide) (alginate-g-(PEOPPO-PEO)), poly(polylactic acid-co-glycolic acid)-co-serine) (P(PLGA-co-serine)), collagen-acrylate, alginate-acrylate, poly(hydroxypropyl methacrylamide-g-peptide) (P(HPMA-g peptide)), poly(hydroxyethyl methacrylate/MATRIGEL gelatinous protein mixture secreted by Engelbreth-Holm-Swarm (EHS) mouse sarcoma cells) (P(HEMA/MATRIGEL gelatinous protein mixture secreted by Engelbreth-Holm-Swarm (EHS) mouse sarcoma cells)), hyaluronic acid-g-N isopropyl acrylamide (HA-g-NIPAAm), polyethylene oxide (PEO), a polyethylene oxide-polypropylene oxide copolymer (PEO-PPO, PLURONIC series), a polyethylene oxide-polylactic acid copolymer (PEO-PLA), a polyethylene oxide-polylactic glycolic acid copolymer (PEO-PLGA), a polyethylene oxide-polycaprolactone copolymer (PEO-PCL), a polyoxyethylene alkyl ethers (BRIJ Series), poly-oxyethylene castor oil derivatives (CREMOPHORE polyoxyethylene castor oil derivatives), polyoxyethylene sorbitan fatty acid esters (TWEEN Series), and polyoxyethylene stearates.

The stent may have an activity inhibiting a proliferation of a blood vessel smooth muscle cell (SMC), an activity increasing adhesion of endothelial cell, or a combination thereof. The stent may have a restenosis-inhibitory activity due to the blood vessel SMC proliferation-inhibitory activity. The stent may have a reendothelialization stimulating activity due to the endothelial cell adhesion increasing activity.

The stent may include a metal, a polymer, or a combination thereof. The metal may include, for example, stainless steel, a nickel-chromium alloy, a nickel-titanium alloy, a cobalt-chromium alloy, platinum-chromium alloy, tantalum, platinum, titanium, nitinol, aluminum, zirconium, chromium, nickel, gold, silver, or a combination thereof. The polymer may include, for example, polylactide, polyglycolide, polycaprolactone, polydioxanone, polylactic-glycolide, or a combination thereof. As used herein, a metal on which nothing is coated is referred to as a bare metal stent.

As used herein, the expression "modified" or "modifying" may refer to that the surface of the stent is coated. The natural polymer may be coated on the surface of the stent by covalent bonding, ionic bonding, metallic bonding, hydrogen bonding, van der Waals interation, physical interaction, or a combination thereof.

According to another aspect of the present disclosure, a method of manufacturing a stent includes: radiating a femtosecond laser onto a surface of a bare metal stent to prepare a femtosecond laser-irradiated stent strut; and modifying a surface of the femtosecond laser-irradiated stent strut with a natural polymer.

In the stent manufacturing method, the terms "femtosecond", the "femtosecond laser", "natural polymer", "modified", "modifying", and "stent" are the same as those described above in connection with the embodiments of the stent.

The method may include radiating a femtosecond laser onto a surface of a bare metal stent to prepare a femtosecond laser-irradiated stent strut.

The femtosecond laser may be a circularly-polarized laser beam or elliptically-polarized laser beam. For example, the femtosecond laser may be a linearly-polarized laser beam.

By the radiating of the femtosecond laser, at least one groove may be formed on the surface of the bare metal stent. The diameter and depth of the groove may be the same as defined above.

By the irradiating of the femtosecond laser onto the surface of the bare metal stent, the surface of the stent strut may be made extremely hydrophobic.

The method may include modifying a surface of the femtosecond laser-irradiated stent strut with a natural polymer.

The modifying with the natural polymer may include incubating the femtosecond laser-irradiated stent strut in the presence of the natural polymer for about 1 day to about 28 days. The incubating may be performed at a temperature of about 20° C. to about 37° C., for example, for about 1 day to about 28 days, about 3 days to about 28 days, about 7 days to about 28 days, about 10 days to about 28 days, or about 14 days to about 28 days. The incubating may be performed at a temperature of about 4° C. to about 37° C., a temperature of about 10° C. to about 37° C., or a temperature of about 20° C. to about 37° C.

The method may include further modifying the stent with a second material with the activity to inhibit restenosis, the activity to stimulate reendothelialization, or a combination thereof. The second material may be a material, a small molecule, or an antibody which are known in the art, or a combination thereof.

One or more embodiments of the present disclosure will now be described in detail with reference to the following examples. However, these examples are only for illustrative purposes and are not intended to limit the scope of the one or more embodiments of the present disclosure.

Example 1: Manufacture of Stent by Femtosecond Laser Radiation and Coating with Hyaluronic Acid, and Effect Thereof Preparation of Femtosecond Laser-Irradiated Stent A bare metal stent made of a cobalt-chromium alloy (18 mm (length)×3.0 mm (inner diameter), available from Minitubes, Grenoble, France) was prepared. The stent was irradiated with an ultra-short femtosecond pulsed laser (available from Light Conversion, Vilnius, Lithuania) having a 6 W maximum power and a center wavelength of about 1,030 nm as a light source. After a laser beam having a diameter of about 2 mm oscillated from the femtosecond laser system was expanded by 5 times using a beam expander, and then passed through a quarter (¼)-wave plate and a linear polarizer for light splitting and polarization control, the laser beam was focused close on the surface of the stent with an object lens (5×, focal length: 40 mm, working distance: 37.5 mm, numerical aperture: 0.14, and depth of focus: 14 µm). A laser spot diameter at the focus was calculated according to using the Gaussian beam equation of $d=4f\lambda_0/n\pi D$, where f is a focal length of the object lens, $\lambda_0$ is a laser beam wavelength, and n is a refractive index. In the present example, the focused laser spot diameter was calculated to be about 4.6 µm with n=1 (refractive index of the air) and D=11.3 mm (objective lens entrance beam diameter), and used as a representative laser spot diameter. A bare metal stent not treated by femtosecond laser irradiation was used as a negative control group.

To avoid the possible dependency of a patterning method upon polarization, the laser beam was polarized into a circular beam on the surface of the stent. A pattern was directly written on each of the stents while the stent was translated using a high-resolution (0.5 mm/pulse) air-bearing X-Y stage and a motor-driven Z stage having a resolution of 1 mm/pulse. The stent was placed in a vacuum chamber mounted on the X-Y-q stage. All patterning processes were monitored in real time with a change-coupled device (CCD)-installed camera. After ultrasonic cleaning of the sample, the machining results were evaluated using an optical microscope and a 3-dimensional (3D) surface profiler. The results of the laser irradiation on the stent through the patterning process were found to be good.

Holes (diameter: 10 μm; depth: 0.1 μm) at regular intervals for drug integration were induced onto the surface of the stent by a femtosecond laser radiation method. The holes were connected by widely dispersed, parallel wave lines.

Coating of Femtosecond Laser-Irradiated Stent with Hyaluronic Acid

The femtosecond laser-irradiated stent strut prepared in the process 1 was coated with hyaluronic acid.

Hyaluronic acid as a natural polymer exhibits an effect of inhibiting growth of blood vessel smooth muscle cells. Accordingly, biocompatibility of a stent may be improved by coating a natural polymer such as hyaluronic acid on the surface of the stent strut.

405 mg of 1-ethyl-3-(3-dimethylaminopropyl)carbodiimide hydrochloride (EDC) and 121 mg of N-hydroxysulfosuccinimide (NHS) were added to a mixed solution of 200 mg of hyaluronic acid and 36 mg of dopamine (in MES, pH 5.5). The reaction product was incubated at about 37° C. for about 8 hours, followed by dialysis at about 37° C. for about 8 hours to remove EDC and NHS and lyophilizing the resulting reaction product for 3 days. The lyophilized reaction product was dissolved in tris-buffered saline (TBS, pH 8.5) to prepare a reaction solution. The stent prepared in the process 1 was then dipped in this reaction solution and incubated at about 37° C. for about 11 hours to thereby prepare a femtosecond laser-irradiated and hyaluronic acid-coated stent.

A bare metal stent coated with hyaluronic acid was used as a control group.

Surfaces of the bare metal stent not treated by femtosecond laser radiation, the femtosecond laser-irradiated stent, and the femtosecond laser-irradiated and hyaluronic acid-coated stent were observed using a scanning electron microscope (SEM, available from Hitachi, Tokyo, Japan).

Figure 1B:
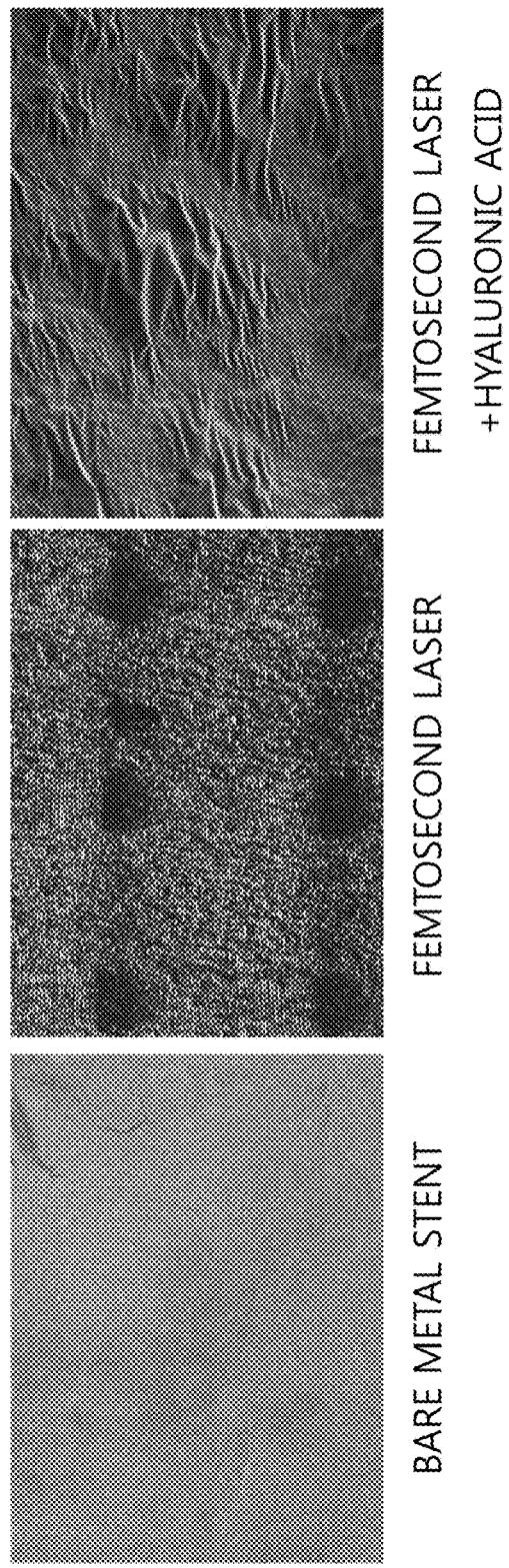

FIG. 1A is a schematic view illustrating a method of preparing a femtosecond laser-irradiated and hyaluronic acid-coated stent of the process 2 according to an embodiment. FIG. 1B exhibits SEM images of the femtosecond laser-irradiated and/or hyaluronic acid-coated stents of the process 2. Referring to FIG. 1B, it was found that hyaluronic acid was coated on the femtosecond laser-irradiated stent strut.

Measurement of Hyaluronic Acid Residence Time of Femtosecond Laser-Irradiated and Hyaluronic Acid-Coated Stent The hyaluronic acid residence time for which hyaluronic acid remained adhered to the femtosecond laser-irradiated and hyaluronic acid-coated stent was measured.

In particular, each of the bare metal stent used in the process 1, the hyaluronic acid-coated metal stent prepared in the process 2, and the femtosecond laser-irradiated and hyaluronic acid-coated stent prepared in the process 2 was soaked in a PBS (available from Sigma-Aldrich) and then incubated at about 37° C. for about 1 day, about 7 days, about 14 days, and about 28 days.

Figure 2:
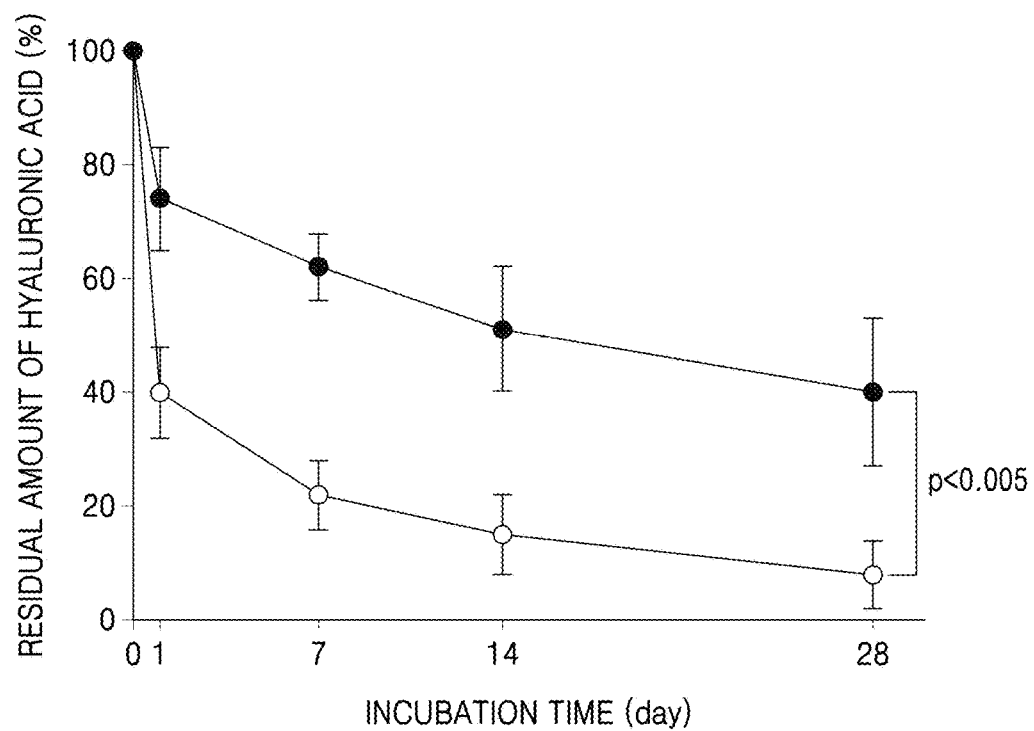
FIG. 2 is a graph of residual amount of hyaluronic acid (%) on the surface of the hyaluronic acid-coated bare metal stent and the surface of the femtosecond laser-irradiated and hyaluronic acid-coated stent with respect to incubation time (○: hyaluronic acid-coated bare metal stent, ●: femtosecond laser-irradiated and hyaluronic acid-coated stent)

The residual amount of hyaluronic acid on the surface of each of the stents was measured by a toluidine blue method. 0.005% (v/v) toluidine blue (in PBS) (available from Sigma-Aldrich) was added to each of the stents, followed by incubation at room temperature with gentile shaking. 200 μl of each of the solutions was taken at each time interval, and absorbances of the solutions at a wavelength of 540 nm were measured using a spectrophotometer. The residual amount of hyaluronic acid (%) on the surface of each stent was calculated from its absorbance. The results are shown in FIG. 2. In FIG. 2, "○" denotes the hyaluronic acid-coated metal stent, and "●" denotes the femtosecond laser-irradiated and hyaluronic acid-coated stent.

Referring to FIG. 2, it was found that hyaluronic acid remained longer in the femtosecond laser-irradiated and hyaluronic acid-coated stent than in the hyaluronic acid-coated metal stent. Accordingly, it was found that the femtosecond laser-irradiated and hyaluronic acid-coated stent has improved biocompatibility due to an increased hyaluronic acid residence time.

Inhibition of Proliferation of Blood Vessel Smooth Muscle Cells in Femtosecond Laser-Irradiated and Hyaluronic Acid-Coated Stent An effect of the femtosecond laser-irradiated and hyaluronic acid-coated stent prepared in the process 2 on the growth of blood vessel smooth muscle cells (SMCs) as a cause of restenosis was investigated.

Figure 3:
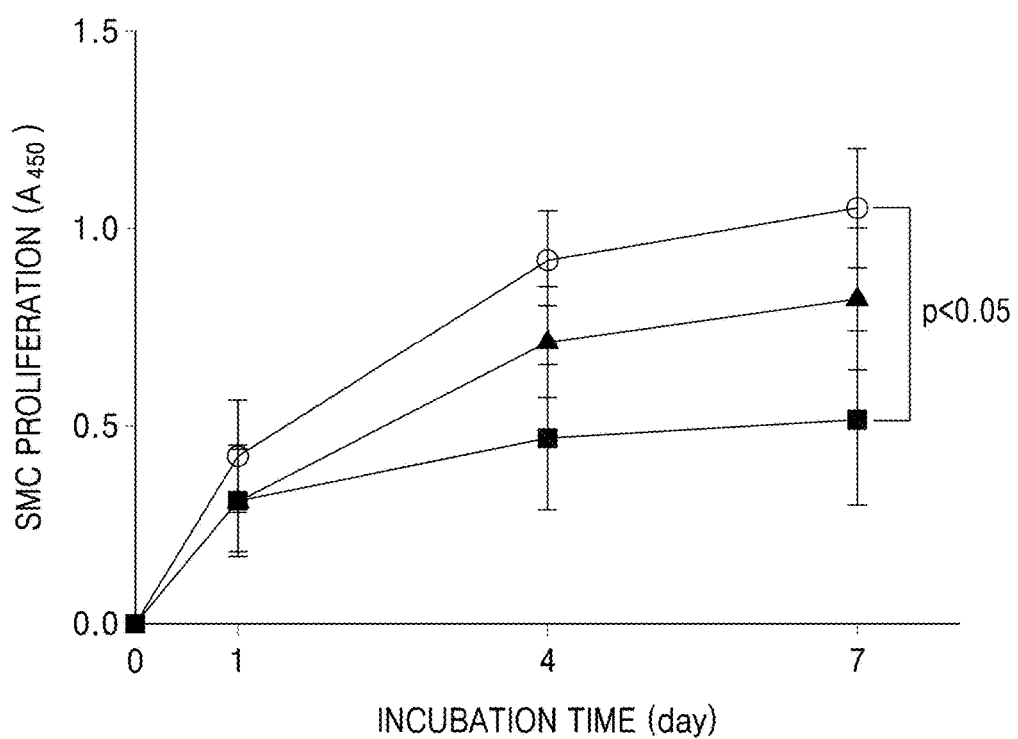
FIG. 3 is a graph of blood vessel smooth muscle cell (SMC) proliferation (absorbance at 450 nm) with respect to incubation time (○: bare metal stent, femtosecond laser-irradiated stent, ■: femtosecond laser-irradiated and hyaluronic acid-coated stent)
Figure 4A:
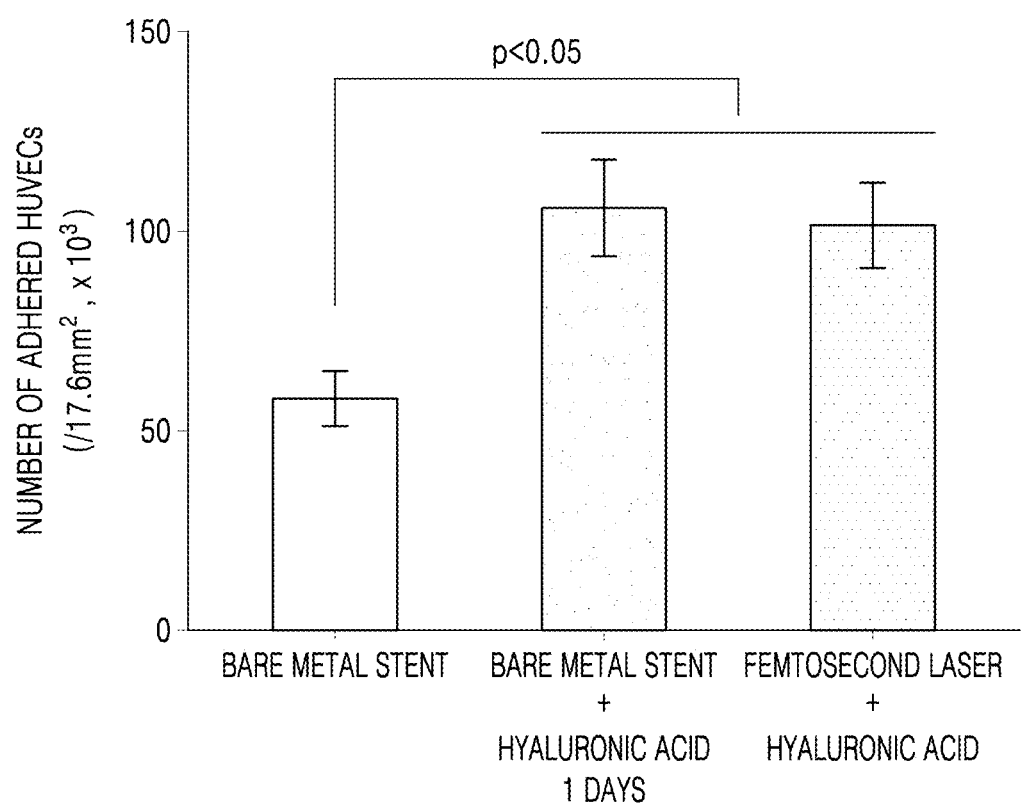
FIGS. 4A to 4D are graphs of the numbers of human umbilical vein endothelial cells (HUVECs) adhered to the bare metal stent, the hyaluronic acid-coated bare metal stent, and the femtosecond laser-irradiated and hyaluronic acid-coated stent after incubation for 1 day, 7 days, 14 days, and 28 days, respectively (NS: not significant).
Figure 4B:
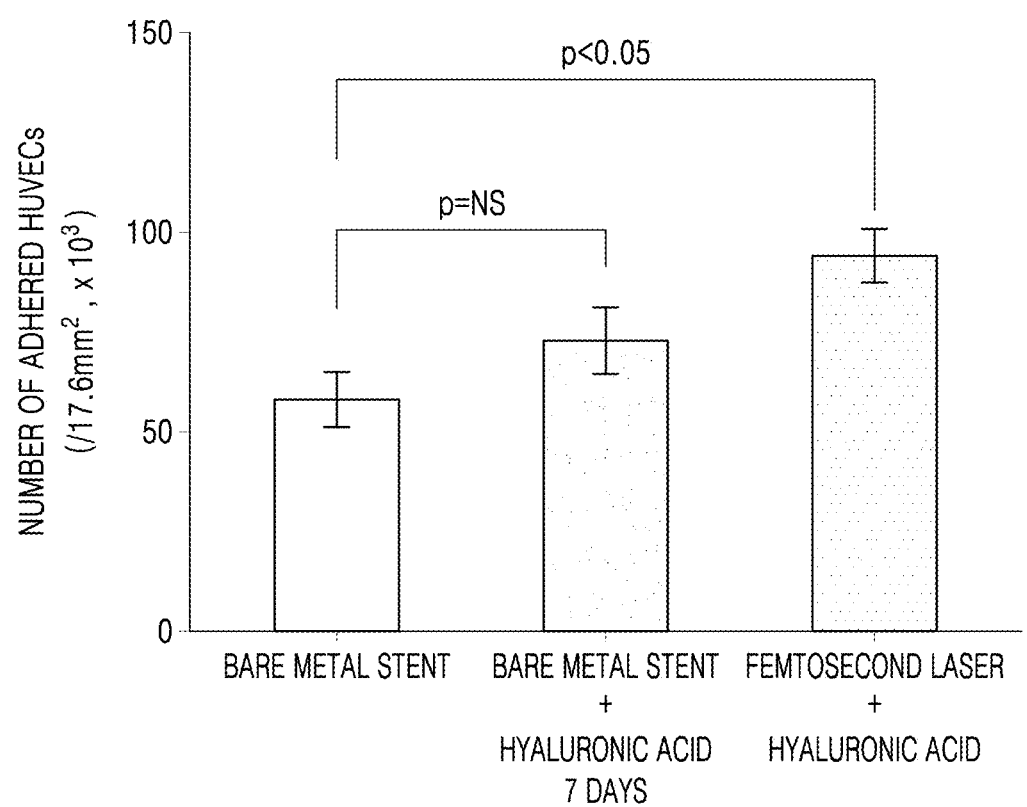
Figure 4C:
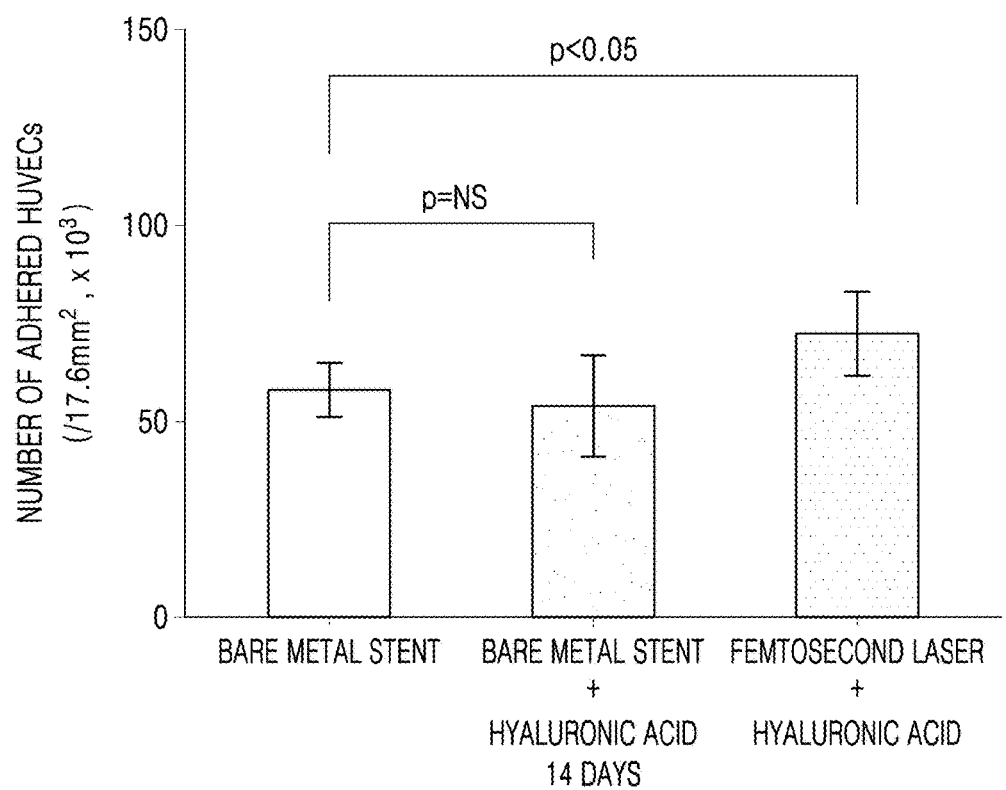
Figure 4D:
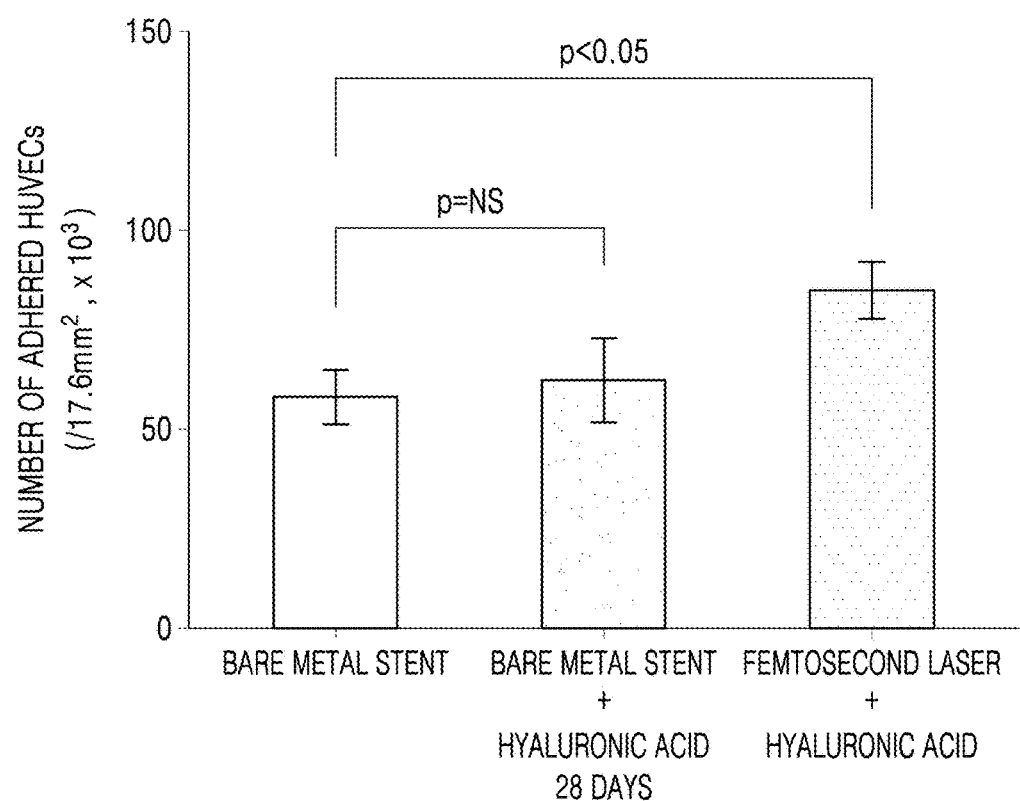

In particular, $5 \times 10^4$ cells/$cm^2$ of blood vessel smooth muscle cells (SMC) were inoculated on a plate. Each of the bare metal stent used in the process 1, the hyaluronic acid-coated metal stent, and the femtosecond laser-irradiated and hyaluronic acid-coated stent prepared in the process 2 was added to the inoculated blood vessel SMCs on the plate, and then incubated under 5% $CO_2$ conditions at about 37° C. for about 7 days, wherein the cell culturing medium was replaced with a fresh medium. The number of grown blood vessel SMC cells was measured from absorbance at 450 nm. The growth of SMCs (absorbance at 450 nm) with respect to incubation time is shown in FIG. 3. In FIG. 3, "○" denotes the bare metal stent, "▲" denotes the femtosecond laser-irradiated stent, and "■" denotes the femtosecond laser-irradiated and hyaluronic acid-coated stent.

Referring to FIG. 3, the femtosecond laser-irradiated stent appears to have a higher blood vessel SMC growth inhibitory effect, though not significant, compared to the bare metal stent. On the other hand, the femtosecond laser-irradiated and hyaluronic acid-coated stent markedly inhibited the growth of SMCs after about 7 days, compared to the bare metal stent. Thus, the femtosecond laser-irradiated and hyaluronic acid-coated stent was found to have a significant effect inhibiting proliferation of blood vessel SMCs.

Endothelial Cell Adhesion to Femtosecond Laser-Irradiated and Hyaluronic Acid-Coated Stent For reendothelialization of a stent in a blood vessel, adhesion of endothelial cells to the stent surface is necessary. An adhering pattern of endothelial cells to the surface of the femtosecond laser-irradiated and hyaluronic acid-coated stent prepared as described in the process 2 was determined.

In particular, each of the bare metal stent used in the process 1, the hyaluronic acid-coated bare metal stent prepared in the process 2, and the femtosecond laser-irradiated and hyaluronic acid-coated stent prepared in the process 2 was soaked in a PBS (available from Sigma-Aldrich) and then incubated at about 37° C. for 1 day, 7 days, 14 days, and 28 days.

$5 \times 10^4$ cells/$cm^2$ of human umbilical vein endothelial cells (HUVECs) were inoculated on a plate. Each of the bare metal stent, the hyaluronic acid-coated bare metal stent, and the femtosecond laser-irradiated and hyaluronic acid-coated stent was added to the inoculated HUVECs on the plate, and then incubated under 5%-$CO_2$ conditions at about 37° C. for about 24 hours, followed by washing out the remaining unadhered cells with PBS. Then, the number of HUVECs adhered to each of the stents was counted using a hematocytometer. The numbers of HUVECs adhered to each of the stents after the incubation for 1 day, 7 days, 14 days, and 28 days are shown in FIGS. 4A to 4D, respectively.

Referring to FIGS. 4A to 4D, the number of adhered HUVECs in the hyaluronic acid-coated metal stent was not significantly different from that in the bare metal stent from the 7-day incubation onwards. However, the number of adhered HUVECs in the femtosecond laser-irradiated and hyaluronic acid-coated stent remained significantly larger than that in the bare metal stent for about 28 days. The metal stent only coated with hyaluronic acid had reduced biocompatibility with time due to easy dissolution of the hyaluronic acid, while the femtosecond laser-irradiated and hyaluronic acid-coated stent had improved biocompatibility due to an increased hyaluronic acid residence time and a large number of HUVECs adhered thereto. Thus, the femtosecond laser-irradiated and hyaluronic acid-coated stent according to an embodiment was found to have a blood vessel reendothelialization effect.

As described above, according to the one or more embodiments, a stent in which a surface of a stent strut is treated by femtosecond laser radiation and is modified by a natural polymer and a method of preparing the stent may inhibit restenosis and stimulate reendothelialization.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the inventive concept as defined by the following claims.

What is claimed is:

1. A stent in which a surface of a stent strut is treated by femtosecond laser radiation and a surface coating of the femtosecond laser-irradiated stent strut consists of one layer of a mixture of a natural polymer and dopamine,
wherein the natural polymer is at least one selected from the group consisting of hyaluronic acid, alginic acid, pectin, carrageenan, chondroitin sulfate, dextran sulfate, chitosan, polylysine, collagen, gelatin, carboxymethylchitin, fibrin, dextran, agarose, pullulan, polyacrylamide (PAAm), poly(Nisopropylacrylamide-co-acrylic acid) (P(NIPAAm-co-AAc)), poly(N-isopropylacrylamide co-ethyl methacrylate) (P(NIPAAm-co-EMA)), polyvinyl acetate/polyvinyl alcohol (PVAc/PVA), poly(N-vinylpyrrolidone) (PVP), poly(methyl methacrylate-co-hydroxyethyl methacrylate) (P(MMA-co-HEMA)), poly(polyethylene glycol-co-peptide) (P(PEG-co-peptide)), alginate-g-(polyethylene oxide-polypropylene oxide-polyethylene oxide) (alginate-g-(PEOPPO-PEO)), poly(polylactic acid-co-glycolic acid)-co-serine), collagen-acrylate, alginate-acrylate, poly(hydroxypropyl methacrylamide-g-peptide) (P(HPMA-g-peptide)), poly(hydroxyethyl methacrylate/gelatinous protein mixture secreted by Engelbreth-Holm-Swarm (EHS) mouse sarcoma cells, hyaluronic acid-g-N-isopropyl acrylamide (HA-g-NIPAAm), polyethylene oxide (PEO), a polyethylene oxide-polypropylene oxide copolymer (PEOPPO), a polyethylene oxide-polylactic acid copolymer (PEO-PLA), a polyethylene oxide-polylactic glycolic acid copolymer (PEO-PLGA), a polyethylene oxide-polycaprolactone copolymer (PEO-PCL), a polyoxyethylene alkyl ethers, polyoxyethylene castor oil derivatives, polyoxyethylene sorbitan fatty acid esters, and polyoxyethylene stearates.

2. The stent of claim 1, wherein the stent has at least one groove on the femtosecond laser-irradiated surface thereof, the at least one groove having a diameter of about 1 μm to about 100 μm and a depth of about 0.01 μm to about 100 μm.

3. The stent of claim 1, wherein the stent has an activity inhibiting a proliferation of a blood vessel smooth muscle cell (SMC), an activity increasing adhesion of endothelial cell, or a combination thereof.

4. A method of manufacturing a stent, the method comprising:
radiating a femtosecond laser onto a surface of a bare metal stent to prepare a femtosecond laser-irradiated stent strut;
applying a coating consisting of one layer of a mixture of a natural polymer and dopamine to a surface of the femtosecond laser-irradiated stent strut; and
incubating the femtosecond laser-irradiated stent in the presence of the mixture of the incubating the coated femtosecond laser-irradiated stent,
wherein the natural polymer is at least one selected from the group consisting of hyaluronic acid, alginic acid, pectin, carrageenan, chondroitin sulfate, dextran sulfate, chitosan, polylysine, collagen, gelatin, carboxymethylchitin, fibrin, dextran, agarose, pullulan, polyacrylamide (PAAm), poly(Nisopropylacrylamide-co-acrylic acid) (P(NIPAAm-co-AAc)), poly(N-isopropylacrylamide co-ethyl methacrylate) (P(NIPAAm-co-EMA)), polyvinyl acetate/polyvinyl alcohol (PVAc/PVA), poly(N-vinylpyrrolidone) (PVP), poly(methyl methacrylate-co-hydroxyethyl methacrylate) (P(MMA-co-HEMA)), poly(polyethylene glycol-co-peptide) (P(PEG-co-peptide)), alginate-g-(polyethylene oxide-polypropylene oxide-polyethylene oxide) (alginate-g-(PEOPPO-PEO)), poly(polylactic acid-co-glycolic acid)-co-serine), collagen-acrylate, alginate-acrylate, poly(hydroxypropyl methacrylamide-g-peptide) (P(HPMA-g-peptide)), poly(hydroxyethyl methacrylate/gelatinous protein mixture secreted by Engelbreth-Holm-Swarm (EHS) mouse sarcoma cells, hyaluronic acid-g-N-isopropyl acrylamide (HA-g-NIPAAm), polyethylene oxide (PEO), a polyethylene oxide-polypropylene oxide copolymer (PEOPPO), a polyethylene oxide-polylactic acid copolymer (PEO-PLA), a polyethylene oxide-polylactic glycolic acid copolymer (PEO-PLGA), a polyethylene oxide-polycaprolactone copolymer (PEO-PCL), a polyoxyethylene alkyl ethers, polyoxyethylene castor oil derivatives, polyoxyethylene sorbitan fatty acid esters, and polyoxyethylene stearates.

5. The method of claim 4, wherein the femtosecond laser is a circularly-polarized laser beam or an elliptically-polarized laser beam.

6. The method of claim 4, wherein the femtosecond laser is a linearly polarized laser beam.

7. The method of claim 4, wherein the incubating is performed for about 1 day to about 28 days.

* * * * *